United States Patent [19]

Asami et al.

[11] Patent Number: 5,410,028

[45] Date of Patent: Apr. 25, 1995

[54] TEST AGENT COMPOSITION FOR DENTISTRY

[75] Inventors: Kuniaki Asami; Fumio Tanaka, both of Tokyo; Ichiro Yamada, Nara, all of Japan

[73] Assignees: Showa Yakuhin Kako Co., Ltd.; Uha Mikakuto Co., Ltd., both of Japan

[21] Appl. No.: 64,115

[22] PCT Filed: Nov. 18, 1991

[86] PCT No.: PCT/JP91/01573

§ 371 Date: May 18, 1993

§ 102(e) Date: May 18, 1993

[87] PCT Pub. No.: WO92/08975

PCT Pub. Date: May 29, 1992

[30] Foreign Application Priority Data

Nov. 19, 1990 [JP] Japan .................. 2-313399

[51] Int. Cl.$^6$ ............................................ G01N 33/50
[52] U.S. Cl. ............................................ 536/2; 424/2; 424/49; 422/68.1; 426/3; 436/63; 436/811; 536/102; 536/114
[58] Field of Search .................. 424/2, 49; 426/3; 436/63, 811; 422/68.1; 536/2, 102, 114

[56] References Cited

U.S. PATENT DOCUMENTS

| | | | |
|---|---|---|---|
| 4,381,318 | 4/1983 | Lynch | 426/658 |
| 4,448,778 | 5/1984 | Lynch | 426/658 |
| 4,471,001 | 9/1984 | Lynch | 426/658 |
| 4,518,581 | 5/1985 | Miyake et al. | 424/49 |
| 4,556,565 | 12/1985 | Arima et al. | 426/658 |
| 4,582,707 | 4/1986 | Calabro | 426/3 |
| 4,587,119 | 5/1986 | Bucke et al. | 424/49 |
| 4,714,620 | 12/1987 | Bunick et al. | 426/804 |
| 4,876,095 | 10/1989 | Yang | 426/3 |
| 4,911,937 | 3/1990 | Crosello et al. | 426/660 |
| 4,963,359 | 10/1990 | Haslwanter et al. | 424/440 |

FOREIGN PATENT DOCUMENTS

| | | |
|---|---|---|
| 0072080 | 2/1983 | European Pat. Off. . |
| 56-6160 | 1/1981 | Japan . |
| 56-35061 | 4/1981 | Japan . |
| 02308759 | 12/1990 | Japan . |

*Primary Examiner*—Ronald W. Griffin
*Attorney, Agent, or Firm*—Cushman Darby & Cushman

[57] ABSTRACT

A test agent composition for dentistry comprises from 5 to 45% by weight of Hydrogenated Maltose Syrup, from 5 to 30% by weight of sorbitol, from 10 to 40% by weight of paratinose, from 5 to 20% by weight of water, from 5 to 37% by weight of a component selected from the group consisting of gelatin, starch and pectin, and from 0.1 to 10% by weight of a detection reagent selected from the group consisting of glucose, vitamins, amino acids, dyes, inorganic salts and other physiologically nontoxic substances, based on the total weight of the composition. The masticatory efficiency of a subject can be evaluated by having the subject chew the test agent composition for dentistry and determining the amount of the detection reagent transferred into the saliva of the subject.

2 Claims, No Drawings

TEST AGENT COMPOSITION FOR DENTISTRY

TECHNICAL FIELD

The present invention relates to a test agent composition for dentistry and a method for testing masticatory efficiency.

BACKGROUND ART

Mastication is conducted by masticatory movements which are made by intricate combinations of the functions of many organs and tissues such as the teeth, periodontal tissues, musculi masticatorii, articulatio temporomandibularises, tongue, labia oris, genae, and salivary secretion organs. Therefore, it is difficult to absolutely and objectively estimate masticatory efficiency.

As one of the conventional methods for testing masticatory efficiency, a method is known which comprises the steps of having a subject put actual food into his mouth, masticate it and spit it out, and then estimating the size of the pieces of masticated food. For example, the subject chews a certain amount of raw rice or peanuts and spits out the chewed food, which is then passed through sieves of certain mesh sizes. The pieces of food on each sieve are dried and weighed. A subject who produces a larger amount of fine chewed food is considered to have higher masticatory efficiency (Comprehensive Dictionary of Dentistry and Medicine, published by ISHIYAKU PUBLISHING CO. LTD., 1988, pp. 1628-1629).

This method for testing masticatory efficiency using raw rice or peanuts described in the above reference is practical in that actual food is used, and the values obtained as a result of the method are persuasive. However, the method has disadvantages in that the procedure is complicated, special tools are necessary, a technician who has mastered the use of the tools is required, it is difficult to standardize the quality of the food, and a large number of tests can not be carried out in a short time.

Other methods have also been developed. In one a piezoelectric element is used to measure biting strength, which is one of the factors of masticatory efficiency, and in another the weak voltage produced in the muscles around the articulatio temporomandibularises is measured. These methods have advantages in that the values obtained are objective and accurate since the biting strength is electrically measured, and that any suitable sensitivity can be selected. However, the methods have disadvantages in that biting strength does not always have a good correlative relation with masticatory efficiency, special tools are necessary for the measurement, and a trained technician is required for the measurement.

Other methods include: the chewing gum method which comprises the steps of having a subject masticate a certain amount of chewing gum containing sugar a certain number of chewing cycles, and measuring the amount of sugar eluted into the saliva; a method which comprises the steps of having a subject masticate granules of adenosine triphosphate disodium (hereinafter referred to as "ATP-G") a certain number of chewing cycles, and determining the amount of ATP-G eluted into the saliva; and the jelly method of estimating a subject's taste for jellies in five grades using several kinds of jellies differing in size and hardness. These methods have advantages in that the procedures for the measurement are simple, the test food can be easily standarized, and the test food is similar to ordinary food. However, the chewing gum method is difficult to use with a subject who wears a full set of dentures. The ATP-G method can not be used for measuring overall masticatory efficiency because the subject unconsciously masticates the granules only at the occlusal portions usually used. The jelly method is an organoleptic test and therefore is not objective. All of the aforementioned methods for testing masticatory efficiency have disadvantages when applied to testing the masticatory efficiency of Japanese subjects since the test food has physical properties different from the foods which Japanese typically prefer but are hard to bite off, such as rubbery vinegared octopus and boiled fish paste. Moreover, the measurements require special instruments such as a photometer that can be operated only by a skilled technician.

DISCLOSURE OF INVENTION

Accordingly, an object of the present invention is to provide a method for testing masticatory efficiency which overcomes the aforementioned disadvantages of the prior art, and a test agent composition for testing masticatory efficiency which can be used for the method.

The method for testing masticatory efficiency of the present invention, which overcomes the above-mentioned disadvantages, was accomplished by the inventors by preparing the test agent composition for dentistry of the present invention.

The present invention provides (1) a test agent composition for dentistry, which comprises from 5 to 45% by weight of Hydrogenated Maltose Syrup, from 5 to 30% by weight of sorbitol, from 10 to 40% by weight of paratinose, from 5 to 20% by weight of water, from 5 to 37% by weight of a component selected from the group consisting of gelatin, starch and pectin, and from 0.1 to 10% by weight of a detection reagent selected from the group consisting of glucose, vitamins, amino acids, dyes, inorganic salts and other physiologically nontoxic substances, based on the total weight of the composition; (2) the aforementioned composition prepared for use in testing masticatory efficiency; and (3) a method for testing masticatory efficiency, which comprises determining the amount of the detection reagent transferred from the composition used for testing masticatory efficiency according to (2) into the saliva of a subject after mastication.

The present invention will hereinafter be explained in detail. The term "mastication" used herein means all physiological processes conducted in the cavum oris and the pharynx after food is put into the mouth up to the time the food is swallowed. The term "masticatory efficiency" means ability of mastication.

A Hydrogenated Maltose Syrup which can be used in the present invention comprises from 75 to 95% by weight of maltitol, from 2 to 15% by weight of Maltotriitol, from 1 to 4% by weight of sorbitol, and the remainder of maltose, preferably comprises from 90 to 95% by weight of maltitol, from 2 to 9% by weight of Maltotriitol, from 1 to 4% by weight of sorbitol, and from 5 to 15% by weight of maltose.

Hydrogenated Maltose Syrup can be prepared as follows:

From 0.1 to 10 units of α-amylase is added to the mixture of 1 part by weight of starch and 10 parts by weight of water, and the resulting mixture is gelatinized at 90°

C. and immediately heated to 130° C. to stop the enzyme reaction. The reaction mixture is rapidly cooled and added with 50 units of pullulanase and 30 units of β-amylase, whereafter the resulting mixture is saccharified for 46 hours to obtain a solution of maltose. The solution is hydrogenated under a hydrogen pressure of from 20 to 100 kg/cm$^2$ at a temperature of from 90° to 125° C. with Ni catalyst. The reaction product is dried to prepare a powder of dried hydrogenated maltose syrup. The dried hydrogenated maltose syrup contains from 25 to 30% of water and is hereinafter referred to as "Hydrogenated Maltose Syrup".

The test agent composition for dentistry of the present invention contains Hydrogenated Maltose Syrup in a content of from 5 to 45% by weight based on the total weight of the composition. If the content of Hydrogenated Maltose Syrup is lower than the above range, the other solid components may be crystallized. If the content of Hydrogenated Maltose Syrup is higher than the above range, the test agent composition may absorb moisture, which makes it difficult to handle due to the stickiness of the surface of the composition. Within the above range, a content of from 20 to 40% by weight is preferred.

A sorbitol which can be used in the present invention is a polyhydroxy alkane obtained by reducing aldose and/or ketose, which contains at least 80% of D-glycitol.

The test agent composition of the present invention contains from 5 to 30% by weight of sorbitol based on the total weight of the composition. If the content of sorbitol is lower than the above range, the test agent composition may become too hard. If the content of sorbitol is higher than the above range, the test agent composition may become too soft. Within the above range, a content of from 10 to 20% by weight is preferred.

Purified water, distilled water, deionized water, and tap water can be used in the present invention. Among these, deionized water is preferred.

The test agent composition for dentistry of the present invention contains from 5 to 20% by weight of water based on the total weight of the composition. If the content of water is lower than the above range, the sugars may be crystallized. If the content of water is higher than the above range, the composition may not be suitable for use in measuring masticatory efficiency because it is too soft, and in some cases, water separation may occur. Within the above range, a content of from 15 to 17% by weight is preferred.

Paratinose, which is also called Isomaltulose, is a disaccharide in which glucose is linked to fructose by α-1,6 linkage. Paratinose can be prepared by reacting saccharose with an enzyme (one of the glycosyltransferases) so that the α-1,2 linkage between glucose and fructose is once cleaved and then a rearrangement reaction occurs which recombines these monosaccharides by α-1,6 linkage.

The test agent composition for dentistry of the present invention contains from 10 to 40% by weight of paratinose based on the total weight of the composition. If the content of paratinose is higher than the above range, the sugar components may be crystallized. If the content of paratinose is lower than the above range, the sweetness of the composition may become less pleasant to the taste and insufficient. Within the above range, a content of from 15 to 30% by weight is preferred.

A gelatin which can be used in the present invention is a denatured collagen found in higher animals, which may comprises lipids and polysaccharides. The molecular weight of the gelatin is in the range of from 15,000 to 250,000. A gelatin having a molecular weight of from 100,000 to 200,000 is preferred.

A starch which can be used in the present invention is α-1,4 glucan which may be contained in storage organs such as seeds and rhizomes of higher plants. The starch comprises from 25 to 27% by weight of amylose and from 75 to 73% by weight of amylopectin and has a molecular weight of from $162 \times 10^3$ to $162 \times 10^5$. In the present invention, corn starch is preferred.

A pectin which can be used in the present invention is a polygalacturonic acid in which some carboxylic groups are methylesterified and which forms a salt with a metalic ion. The molecular weight of the pectin is in a range of from 50,000 to 200,000. Specific examples of the metalic ions include sodium and potassium ions. A pectin having a ratio of methylesterification of from 4.1 to 5.8% and a molecular weight of from 50,000 to 200,000 is preferred.

The test agent composition for dentistry of the present invention contains from 5 to 37% by weight of one or more components selected from the group consisting of gelatin, starch and pectin based on the total weight of the composition. If the content of the above components is lower than the above range, the hardness, gum properties and adhesion properties of the composition may become inappropriate. If the content of the above composition is higher than the above range, the hardness, gum properties and adhesion properties of the composition may become so high that the composition becomes rubbery. Within the above range, the composition preferably contains from 5 to 20% by weight of gelatin based on the total weight of the composition. The composition more preferably contains from 10 to 15% by weight of gelatin, from 0 to 3% by weight of starch and from 0 to 1.5% by weight of pectin.

A detection reagent which can be used in the present invention is selected from the group consisting of glucose, vitamins, amino acids, dyes, inorganic salts and other physiologically nontoxic substances. Specific examples of the vitamins include vitamin A, vitamin C, vitamin $B_1$, vitamin $B_2$, and mixtures thereof. Specific examples of the amino acids include glycine, alanine, lysine, histidine, leucine, and mixtures thereof. Any dye which can be added to food may be used, including synthetic dyes such as red No.2, red No.3, yellow No.5, blue No.1 and blue No.2, and natural dyes such as safflower, annatto, anthocyanin, gardenia, chlorophyll, carotene, curcumin, cochineal and the like. Specific examples of the inorganic salts include physiologically and relatively nontoxic ones such as hydrochlorides, nitrates, and acetates of sodium, potassium, magnesium or calcium. The term "physiologically nontoxic substances" used herein means substances which are physiologically nontoxic in the amount used. Specific examples of physiologically nontoxic substances include riboflavin, sodium benzoate, amino acids, and chlorophyll. Among these detection agents, glucose and vitamin C are preferred.

The test agent composition for dentistry of the present invention contains from 0.1 to 10% by weight of the detection reagent based on the total weight of the composition. If the content of the detection reagent is lower than the above range, special instruments which can be operated only by a skilled technician may be required as detectors. If the content of the detection reagent is higher than the above range, the hardness and viscosity of the test agent composition may not be sufficiently adjustable. Within the above range, the content of the detection reagent is preferably from 0.1 to 5% by weight.

The detection reagent may be present as uniformly dissolved in the composition, or as encapsuled in microcapsules prepared with gelatin and/or other components, which are dispersed in the composition. With regard to microcapsules and gelatin capsules, the techniques described in "New Technique of Microcapsulization and Development of Use Thereof: Application Examples" edited by KEIEI KYOIKU DIVISION and published by KEIEI KAIHATSU CENTER PUBLISHING DEPARTMENT, 1978, and those described in "Pharmacological Knowledge and Prescription Collection of Suppository", Yozo Shintani, Dispensary, vol.32, No.10, p. 1234 can be used.

The test agent composition for dentistry of the present invention may contain additives such as sodium citrate, cyclodextrin, erythritol, saccharin and the like. The content of these additives is preferably 0.01 to 20% by weight based on the total weight of the composition.

The test agent composition for dentistry of the present invention may contain from 1/200 to 1/2000 parts by weight of flavorings such as herb flavorings (peppermint, eucalyptus and the like), and fruit flavorings (pineapple, strawberry, lemon and the like) based on the total weight of the composition.

One embodiment of the test agent composition for dentistry of the present invention is as follows:
In 100 g of the composition,

| Hydrogenated Maltose Syrup | 15–25 g |
|---|---|
| Sorbitol | 10–18 g |
| Paratinose | 20–35 g |
| Water | 10–20 g |
| Gelatin | 5–20 g |
| Starch | 3–7 g |
| Pectin | 2–6 g |

The shape of the particles or pieces of the test agent composition for dentistry of the present invention is not specifically limited. Typical examples of acceptable shapes include spherical, ovoid, hexahedron, sheet, polyhedron and the like. Among these, ovoid, spherical, and shapes similar thereto are preferred.

The weight of one piece of the test agent composition for dentistry of the present invention may be from 0.01 to 7 g, preferably from 0.05 to 5 g.

One example of a method of preparing the test agent composition for dentistry of the present invention will be explained. A heated aqueous solution comprising all components of the composition of the present invention is prepared. Concavities are formed on dried corn starch by pressing with a plaster or metalic mold. The solution is poured into the concavities and then dried. The dried composition is removed from the corn starch and adhered corn starch is removed from the composition by shaking.

The test agent composition for dentistry of the present invention prepared as described above preferably has physical properties such as from 100 to 200 of hardness (g) under 4 mm of compression stress, from 0.5 to 1.5 of softness (cm/dyn), from $1,000 \times 10^4$ to $2,000 \times 10^4$ of Young's modulus of elasticity (dyn/cm$^2$), from 50 to 100 of crispness, and from 20,000 to 30,000 of breaking strength (g/cm$^2$).

The aforementioned physical properties can be measured by a NRM-2010J-CW rheometer available from FUDO INDUSTRY Co. Ltd., using 5 mm $\phi$ adapter at a speed of 6 cm/minute at a room temperature (20° C.).

The test agent composition for dentistry of the present invention can be used for testing masticatory efficiency and training for improving masticatory efficiency.

In the method for testing masticatory efficiency of the present invention, a subject puts one or more, preferably from 1 to 3, pieces of the test agent composition for dentistry into his mouth and masticates the composition from 5 to 20 chewing cycles, preferably from 8 to 15 chewing cycles. The speed of mastication may be from 0.8 to 2 chewing cycles/second, preferably from 1.1 to 1.4 chewing cycles/second.

After the completion of mastication, the test agent composition for dentistry and the saliva are collected from the subject and the quantity of the detection agent transferred into the saliva of the subject is determined. Alternatively, after the completion of mastication, the test agent composition for dentistry and the saliva are collected from the subject. Then, the subject washes out his mouth using 10 ml of water, the water used for washing is mixed with the mixture of the test agent composition for dentistry and the saliva, and the quantity of the detection reagent contained in the resulting mixture is determined. In another method, immediately after the completion of mastication, the subject washes out his mouth using 10 ml of water and the mixture consisting of the test agent composition for dentistry, the saliva and the water are collected from the subject to determine the quantity of the detection reagent in the mixture.

The masticated test agent composition for dentistry is preferably collected in a container printed on the bottom surface with measure or grid lines which enable the subject to observe the state of the masticated test agent composition pieces and thus judge his masticatory efficiency. This is useful for motivating subjects to improve their masticatory efficiency. The bottom surface of the container may be of any shape such as circular, polygonal (including triangular and rectangular), and is preferably flat. The container preferably has a bottom area of from 9 to 30 cm$^2$. For example, if the bottom surface is circular, the diameter thereof is preferably from 4 to 10 cm and if it is rectangular, the sides preferably measure from 3 to 10 cm. The height of the container is preferably from 3 to 10 cm. The color of the container is preferably white. The interval between the measure or grid lines is preferably from 7 to 15 mm, more preferably about 10 mm. The width of the measure or grid lines is preferably from 0.5 to 1 mm and the color of the measure or grid lines is preferably a color contrasting with white, such as black, dark brown, dark blue or the like.

Specific examples of the methods of determining the quantity of the detection reagent transferred into the saliva of the subject include an absorbance method of measuring the absorbance at a certain absorption wavelength, a method comprising the steps of immersing a piece of paper containing a color producing reagent into the collected saliva and visually estimating the color tone of the paper after coloring using a standard colorimetry table, a method of visually and directly estimating the color tone of the saliva colored with the transferred dye using a standard colorimetry table, or the like.

If glucose is used as the detection reagent, the quantity of the detection reagent transferred into the saliva of the subject can be determined by visual colorimetry or absorbance colorimetry using cumene reaction, Somogyi's reaction, anthrone reaction, glucose oxidase method, ortho-tolidine-boric acid method, or the like.

If amino acid is used as the detection reagent, the quantity of the detection reagent transferred into the saliva of the subject can be determined by an absorbance method of measuring the absorbance at a wavelength in the ultraviolet region or by visual colorimetry using ninhydrin reaction, Millon reaction, biuret reaction or the like.

If a dye is used as the detection reagent, the quantity of the detection reagent transferred into the saliva of the subject can be determined by measuring the absorbance at the absorption wavelength of the dye. For example, absorbance of red No.2 is measured at 520 nm, absorbance of red No.3 is measured at 526 nm, absorbance of yellow No.5 is measured at 480 nm, absorbance of blue No.1 is measured at 630 nm and absorbance of blue No.2 is measured at 612 nm.

Furthermore, the quantity of the detection reagent transferred into the saliva of the subject can be determined by visual colorimetry of the color of the saliva into which the dye is transferred.

In the method for testing masticatory efficiency of the present invention, the amount of the test agent composition for testing masticatory efficiency, the number of chewing cycles and the speed of mastication can be suitably varied depending on the age, the sex and the like of the subject.

The method for testing masticatory efficiency of the present invention makes it possible to measure masticatory efficiency simply. As a result, a large number of subjects can be tested for masticatory efficiency in a short time.

The method for testing masticatory efficiency of the present invention makes measurement of masticatory efficiency compatible with Japanese eating habits possible.

The method for testing masticatory efficiency of the present invention makes it possible to ascertain the state of the molars, the functioning of prosthetic devices such as dentures, masticatory habits and the like.

BEST MODE FOR CARRYING OUT THE INVENTION

A detailed explanation of the present invention will be made with reference to examples. These examples are not intended to limit the scope of the present invention.

EXAMPLE 1

| | |
|---|---|
| Hydrogenated Maltose Syrup | 115 g(about 27.0% by weight) |
| Sorbitol | 70 g(about 16.4% by weight) |
| Paratinose | 100 g(about 23.4% by weight) |
| Gelatin | 40 g(about 9.4% by weight) |
| Erythritol | 50 g(about 11.7% by weight) |
| Glucose | 1.5 g(about 0.4% by weight) |
| Water | about 50 ml(about 11.7% by weight) |

Hydrogenated Maltose Syrup, sorbitol, paratinose, gelatin and erythritol were added to about 50 ml of water and dissolved therein by heating to 180° C. One point five grams of glucose was added to 300 g of the resulting solution and the mixture was stirred at 95° C. for 3 minutes.

Using the so-obtained solution, the composition was prepared in flat, oval pieces each weighing about 4 g and having a surface area of about 3.4 cm². The weight of the glucose contained in each piece was about 20 mg.

EXAMPLE 2

| | |
|---|---|
| Hydrogenated Maltose Syrup | 115 g(about 42.1% by weight) |
| Sorbitol | 70 g(about 25.6% by weight) |
| Gelatin | 40 g(about 14.6% by weight) |
| Starch | 15 g(about 5.5% by weight) |
| Pectin | 2 g(about 0.7% by weight) |
| Glucose | 1.4 g(about 0.5% by weight) |
| Water | 30 ml(about 11.0% by weight) |

The procedures of Example 1 were repeated except that the above composition was used. The composition was prepared in flat, oval pieces each weighing about 4 g and having a surface area of about 3.4 cm². The weight of the glucose contained in each piece was about 20 mg.

EXAMPLE 3

| | |
|---|---|
| Hydrogenated Maltose Syrup | 70 g(about 16.3% by weight) |
| Sorbitol | 70 g(about 16.3% by weight) |
| Paratinose | 150 g(about 35.0% by weight) |
| Fructose | 10 g(about 2.3% by weight) |
| Gelatin | 65 g(about 15.2% by weight) |
| Starch | 10 g(about 2.3% by weight) |
| Pectin | 2 g(about 0.5% by weight) |
| Glucose | 1.9 g(about 0.4% by weight) |
| Water | 50 ml(about 11.7% by weight) |

The procedures of Example 1 were repeated except that the above composition was used. The composition was prepared in flat, oval pieces each weighing about 4 g and having a surface area of about 3.4 cm². The weight of the glucose contained in each piece was about 20 mg.

EXAMPLE 4

| | | |
|---|---|---|
| A | Water | 50 ml |
| | Propylene glycol | 10 ml |
| | Glucose | 15 g |
| B | Gelatin | 5.5 kg |
| | Glycerin | 4.0 kg |
| | Sorbitol | 2.5 kg |
| | Water | 35.0 kg |
| C | Hydrogenated Maltose Syrup | 130 g(about 18.5% by weight) |
| | Sorbitol | 140 g(about 20.0% by weight) |
| | Paratinose | 200 g(about 28.5% by weight) |
| | Gelatin | 80 g(about 11.4% by weight) |
| | Erythritol | 50 g(about 7.1% by weight) |
| | Glucose | 1.5 g(about 0.2% by weight) |
| | Water | 70 ml(about 10.0% by weight) |
| | Propylene glycol | 30 ml(about 4.3% by weight) |

Using a solution having composition A as a core, gelatin spheres encapsuled with gelatin membranes were prepared using the solution having composition B according to methods described in "Pharmacological Knowledge and Prescription Collection of Suppository", vol.32, No.10, p.1234. About 40,000 gelatin spheres each weighing about 2 mg were obtained. In each gelatin sphere, the weight of the gelatin membrane was 0.8 mg and the weight of the glucose solution was about 1.2 mg.

A solution having composition C was prepared using the procedure of Example 1 and cooled to a temperature of from 75° to 80° C. The gelatin spheres were added to the solution in a concentration of about 2.0% by weight and the mixture was stirred. Immediately thereafter, the mixture was casted in a mold and cooled.

Pieces shaped like rugby balls and each weighing about 5 g were obtained. The weight of the glucose contained in each piece was about 20 mg.

EXAMPLE 5

Two healthy adult males, A (52 years old) and B (45 years old), who had normal occlusion and showed no abnormality in the function of their jaws and cavum orises were tested for masticatory efficiency as follows: Each subject put one piece prepared in Example 1 in his mouth and masticated it slowly in the same manner as when eating an ordinary meal. The speed of mastication was 10 chewing cycles/8 seconds. After 10 chewing cycles of mastication, he spit out the masticated pieces and his saliva into a paper cup. Test paper for glucose "Salivastar (registered trademark) GLU" available from Showa Yakuhin Kako Co., Ltd. was immersed in the saliva and brought out after 3 seconds. The excess saliva on the test paper was wiped off with tissue paper and after 30 seconds colorimetry of the tone of the blue color produced on the test paper by development was carried out using a standard colorimetry table (20, 50, 100, 200 and 300 mg/dl).

The above procedure was repeated except that the number of chewing cycles of mastication was set at 5, 20, or 40.

The results of the above tests are shown in Table 1.

TABLE 1

|  | A | B |
|---|---|---|
| 5 chewing cycles of mastication | 20 | 20 |
| 10 chewing cycles of mastication | 100 | 100 |
| 20 chewing cycles of mastication | 200 | 200 |
| 40 chewing cycles of mastication | 300 | 300 |
|  |  | (mg/dl) |

The above results show that in the range of from 10 to 20 chewing cycles, the amount of glucose eluted from the composition is proportional to the number of chewing cycles of mastication.

EXAMPLE 6

Ten adult subjects were tested for masticatory efficiency using the same procedure as that of Example 5 at 20 chewing cycles of mastication at a mastication speed of 20 chewing cycles/16 seconds.

The masticatory efficiency test was repeated three times for each subject. The interval between tests was at least 10 minutes and the subject rinsed his mouth several times with tap water just before each test.

Condition of Subject's Teeth

The cavum orises of the subjects were observed in the light of the subjects' statements.

| No. | Age | Condition of Teeth in Cavum Oris |
|---|---|---|
| 1 | 65 years old | Although there were several restored teeth, he had a full set of teeth and no dentures. The opposing teeth were well engaged. |
| 2 | 52 | Although there were several restored teeth, he had a full set of teeth and no dentures. The opposing teeth were well engaged. |
| 3 | 45 | Although there were several restored teeth, he had a full set of teeth and no dentures. The opposing teeth were well engaged. |
| 4 | 24 | Although there were several restored teeth, he had a full set of teeth and no dentures. The opposing teeth were well engaged. |
| 5 | 60 | The upper right first and second molars and the upper left first and second molars were dentures and the other were natural teeth. |
| 6 | 70 | The upper teeth were a full set of dentures and the lower anterior teeth were dentures. |
| 7 | 73 | Both of the upper teeth and the lower teeth were full sets of dentures. |
| 8 | 68 | The upper teeth were a full set of dentures, and the lower teeth other than the second molar, the right first and second premolars were dentures. |
| 9 | 20 | He had a full set of teeth. |
| 10 | 47 | Although he had a full set of teeth, both of the upper anterior teeth and the lower anterior teeth were loose. |

Subjects' Eating Habits

Information about the subjects' eating habits was obtained by oral questioning.

| No. |  |
|---|---|
| 1 | Eats tough foods chewing them well. |
| 2 | Eats tough foods chewing them well. |
| 3 | Eats tough foods chewing them well. |
| 4 | Eats any kind of food in spite of disliking of tough foods |
| 5 | Feels that he can chew tough foods as though he had a full set of teeth. |
| 6 | Eats any kind of food and chews tough foods well. |
| 7 | Has trouble chewing pickled radishes, one of his favorite foods. |
| 8 | Eats tough foods with difficulty, chewing them well. |
| 9 | Rarely eats tough foods; prefers soft foods. |
| 10 | Rarely eats tough foods and, when he does, takes a long time to eat them since his teeth are loose. |

The results of the masticatory efficiency tests are shown in Table 2.

TABLE 2

| No. | Eluted Glucose Amount (mg/dl) | | | | Masticatory Efficiency (%)* |
|---|---|---|---|---|---|
|  | $n_1$ | $n_2$ | $n_3$ | n |  |
| 1 | 300 | 300 | 300 | 300 | 100 |
| 2 | 300 | 300 | 300 | 300 | 100 |
| 3 | 300 | 300 | 300 | 300 | 100 |
| 4 | 300 | 300 | 300 | 300 | 100 |
| 5 | 300 | 200 | 200 | 230 | 78 |
| 6 | 100 | 200 | 200 | 170 | 56 |
| 7 | 20 | 20 | 50 | 30 | 10 |
| 8 | 20 | 50 | 50 | 40 | 13 |
| 9 | 300 | 300 | 300 | 300 | 100 |
| 10 | 100 | 50 | 50 | 70 | 22 |

*Masticatory efficiency is represented by percentage of the amount of eluted glucose based on 300 mg/dl of eluted glucose as 100%.

Subjects 1–4 who were considered to have good teeth and good eating habits had 100% of masticatory efficiency.

Subject 9 who did not like tough foods had excellent masticatory efficiency (100%) and therefore was evaluated to have the ability to eat tough foods. This is probably because he is young.

Subject 5 whose upper molars were dentures had high masticatory efficiency (78%) which is consistent with his statement that he can chew tough foods without difficulty.

Subject 10, who is 47 years old, did not seem to chew the composition well by turning it over in his mouth, probably because his anterior teeth were loose. The masticatory efficiency of 22% is consistent with his statement that he rarely eats tough foods as part of his daily meals.

Subjects 7 and 8 did not seem to be able to chew the composition. Their masticatory efficiencies were 10% and 13%, respectively. They stated that they cut tough foods into small pieces and swallow them without chewing.

It is seen that the results obtained by the method for testing masticatory efficiency of the present invention agree with the masticatory efficiencies presumed from the conditions of the subjects' teeth and the subjects' statements about their eating and chewing habits. The results clearly reflect the conditions of the molars and the premolars which are the usual occlusal portions, the functioning of prosthetic devices such as dentures, the masticatory habits, and the like.

Industrial Applicability

The test agent composition for dentistry of the present invention can be used for evaluating masticatory efficiency.

We claim:

1. A test agent composition for dentistry, which comprises from 5 to 45% by weight of Hydrogenated Maltose Syrup, from 5 to 30% by weight of sorbitol, from 10 to 40% by weight of paratinose, from 5 to 20% by weight of water, from 5 to 37% by weight of a component selected from the group consisting of gelatin, starch and pectin, and from 0.1 to 10% by weight of a detection reagent selected from the group consisting of glucose, vitamins, amino acids, dyes, inorganic salts and other physiologically nontoxic substances, based on the total weight of the composition.

2. A method for testing masticatory efficiency, which comprises the following steps:
- putting one or more pieces of the composition according to claim 1 into a subject's mouth in which the weight per piece of the composition is from 0.05 to 5 g;
- masticating the composition by said subject, from 5 to 20 chewing cycles at the mastication speed from 0.8 to 2 chewing cycles/second;
- determining the quantity of the detection agent transferred into the saliva of the subject; and
- evaluating the masticatory efficiency by the amount of eluted detection agent.

* * * * *